United States Patent
Landis et al.

(10) Patent No.: US 7,033,075 B2
(45) Date of Patent: Apr. 25, 2006

(54) APPARATUS FOR RETAINING A RADIOGRAPHIC SENSOR DURING DENTAL X-RAY IMAGING

(75) Inventors: Timothy J. Landis, Granite Bay, CA (US); Clay D. Allen, Wilton, CA (US)

(73) Assignee: OP-D-OP, Inc., Roseville, CA (US)

( * ) Notice: Subject to any disclaimer, the term of this patent is extended or adjusted under 35 U.S.C. 154(b) by 183 days.

(21) Appl. No.: 10/724,001

(22) Filed: Nov. 25, 2003

(65) Prior Publication Data

US 2004/0170253 A1 Sep. 2, 2004

Related U.S. Application Data

(60) Provisional application No. 60/429,721, filed on Nov. 27, 2002.

(51) Int. Cl.
*A61B 6/14* (2006.01)
(52) U.S. Cl. ...................................... 378/168; 378/170
(58) Field of Classification Search ............... 378/168, 378/187, 189–191, 167–170; 206/455
See application file for complete search history.

(56) References Cited

U.S. PATENT DOCUMENTS 3,473,026 A * 10/1969 Updegrave .................. 378/170
6,203,195 B1 * 3/2001 Willis ......................... 378/168
6,540,399 B1 * 4/2003 Eppinger et al. ........... 378/170

* cited by examiner

*Primary Examiner*—David V. Bruce
*Assistant Examiner*—Hoon Song
(74) *Attorney, Agent, or Firm*—John P. O'Banion

(57) ABSTRACT

A radiographic sensor retention apparatus for retaining a radiographic sensor and allowing it to be properly positioned within the mouth of a dental patient during x-ray image registration. The apparatus is held in position within the mouth of the patient in response to biting pressure from the upper and lower dental surfaces, and comprises a bite block with an extending first jaw member, a second jaw member slidably engaged with the bite block, and a threadable member connecting the second jaw member to either the bite block or the first jaw member, wherein the separation between the jaws is continuously variable in response to the rotation of the threadable member. Compliant members are preferably joined to one or both of the jaw members to aid in distributing the retention forces and to reduce sensor slippage. The bite block is preferably configured for the attachment of at least one alignment guide.

38 Claims, 8 Drawing Sheets

APPARATUS FOR RETAINING A RADIOGRAPHIC SENSOR DURING DENTAL X-RAY IMAGING

CROSS-REFERENCE TO RELATED APPLICATIONS

This application claims priority from U.S. provisional application Ser. No. 60/429,721 filed on Nov. 27, 2002, incorporated herein by reference in its entirety.

STATEMENT REGARDING FEDERALLY SPONSORED RESEARCH OR DEVELOPMENT

Not Applicable

REFERENCE TO A COMPUTER PROGRAM APPENDIX

Not Applicable

BACKGROUND OF THE INVENTION

1. Field of the Invention

The present invention generally pertains to dental x-ray equipment, and more particularly to an apparatus for retaining a radiographic sensor adjacent to a bite block held between the teeth of a patient during dental x-ray image registration.

2. Description of the Background Art

The registration of radiographic data during dental x-ray imaging utilizes a radiographic sensor that must be retained in a desired position within the mouth of the patient and in a fixed relationship to the dental structures for which images are sought. A radiographic emitter (x-ray source unit) is then aligned with the radiographic sensor and a brief pulse of x-ray radiation is generated that is registered upon the radiographic sensor, communicated to a processor, and displayed as an x-ray image.

Radiographic sensor retention (holder) devices are utilized for retaining the radiographic sensor in a desired position while capturing various dental x-ray images. These devices may be utilized for capturing x-ray images of any dental structures, for example anterior bite wings, posterior bite wings, or even in preparation for endodontic surgery. The described radiographic retention devices also operate to prop open the mouth of the patient for providing proper separation between the upper and lower jaws and associated dental structures. A number of sensor retention devices have been implemented for performing these functions. One such device being described in U.S. Pat. No. 6,203,195 issued Mar. 20, 2001, which is included herein by reference.

The radiographic retention device described within the referenced patent utilizes a friction held clasp mechanism held in a particular position by interlocking ratcheted teeth. The radiographic sensor may be retained within the ratcheted clasp mechanism subject to a limited number of discrete retention positions. Utilizing this ratcheted form of friction retention mechanism results in a number of drawbacks. It is difficult to make close tolerance adjustments to the clasp due to the discrete positioning provided by the ratchet teeth. Size adjustment is difficult while manually holding a radiographic sensor within the clasp while it is being secured. Furthermore, the clasp mechanism is subject to disengagement, wherein the radiographic sensor may fall loose within the mouth of the patient, or may even fall to the floor prior to being positioned in the patient's mouth.

Therefore, a need exists for a an x-ray sensor retention apparatus that provides secure retention, convenient adjustability, and which is suitable for use with a number of different sensor packages. The present invention satisfies those needs, as well as others, and overcomes the deficiencies of previously developed x-ray sensor retention devices.

BRIEF SUMMARY OF THE INVENTION

A radiographic sensor retention apparatus is described having jaws which extend from a bite block that is configured for securing a radiographic sensor. Distance between the jaws of the retention apparatus is controlled by a continuously variable threaded screw clamp. The retention apparatus is configured for being held in response to biting forces between upper and lower teeth, or jaws. The apparatus may be utilized as embodied herein, or reshaped to fit any oral cavity location for collecting images of the associated dental structures, such as from anterior bite wing positions back through posterior bite wing positions, without departing from the teachings of the present invention. While receiving a short burst of low-level x-ray radiation, the radiographic sensor within the patients mouth captures and communicates a radiographic image to a computer or other digital recorder which displays the associated x-rays of the dental structures.

The sensor retention apparatus may be configured with one or more alignment guides that provide a positional reference when aligning the radiographic emitter device with the radiographic sensor within the mouth of a patient. A ring alignment guide and an extended arm alignment guide are described herein by way of example.

The sensor retention apparatus generally comprises a bite block; a first jaw member extending from the bite block; a movable second jaw member in opposition to the first jaw member; and means for providing continuously variable positional adjustment of the second jaw member in relation to the first jaw member for the secure retention of a radiographic sensor which may be inserted between said first and second jaw members. The means for providing continuously variable positional adjustment of the jaw members allows incremental adjustment of the distance between the second jaw member and the first jaw member to assure proper retention of a radiographic sensor. The means for providing continuously variable adjustment preferably comprises a threaded member interconnecting the jaw members. An input receiving member, such as an adjustment knob, head, or crank, may be attached to the threaded member to increase leverage and thereby increase the available torque upon the threaded member.

The apparatus may incorporate a means for aligning an external radiographic emission source with radiographic sensor being retained in the mouth of a patient. By way of example, the alignment means may comprise an elongated member extending from the bite block to provide a positional reference to speed the alignment process. Alignment guides of various configurations may be provided for attachment upon the elongated member to further aid alignment.

The sensor retention apparatus may be manufactured from any convenient material although polymeric materials, such as moldable thermoplastics, are preferred. The preferred method of manufacture is by injection molding, although any convenient method for creating a three-dimensional structure may be employed. The exterior of the bite block may be adapted with structures and/or material for engaging and assuring comfortable retention between the teeth. By way of example, protrusions may extend from the bite block for engaging dental structures while compressible materials may be additionally, or alternatively, utilized to increase securement and comfort.

By way of example, the sensor retention apparatus may be implemented with a first jaw member extending from the bite block near a distal end. A second jaw member within a jaw assembly being movably retained in relation to the bite block, such as near the distal end of the bite block. The movable structure of the second jaw member in combination with the first jaw member may be considered to comprise a clasping mechanism for retaining a radiographic sensor.

A threaded member provides continuous adjustment of jaw closure, which may be contrasted with non-continuous fixed position for jaw closure such as provided by conventional ratcheted clasp mechanisms. Continuous adjustability refers to the ability to set the position of the jaws at any desired distance (or retention pressure) within the range of jaw movement. The continuously variable adjustment provided by the present invention thereby allows a wide range of sensors to be properly retained between the jaws at a precisely regulated retention pressure. The means for providing continuously variable adjustment preferably comprises a threaded member that attaches between the bite block (or first jaw member, or other structures extending therefrom), and the second movable jaw member.

A rotational input receiving member is preferably implemented as a manual control joined to the threaded member for receiving user input, which by way of example may comprise a knob, wheel, crank, or other rotational input which provides leverage to generate a torque on the threaded member which is converted by the jaws to create a sufficient retention pressure between the movable second jaw member and the stationary first jaw member. The manual control is preferably implemented as a knob attached to a terminating end of the threaded member. The separation distance between the jaws is thereby adjusted by rotating the threaded member in either of two rotational directions for properly retaining a radiographic sensor securely between the jaws of the unit while radiographic images are being registered from within the mouth of the patient.

Compliant materials, such as compressible material pads, or the like, may be joined to at least a portion of the inner surfaces of one or both jaw members to distribute the compression forces being applied to the radiographic sensor and for preventing the sensor from slipping out from the jaws.

An alignment guide may optionally extend from the bite block as a positional reference so that one may readily and accurately align a radiographic imaging emission source with the radiographic sensor whose position is substantially obscured within the mouth of the patient. The alignment guide may comprise an elongated member that is either permanently or removably joined to the bite block.

The sensor retention device of the present invention is an improvement of radiographic sensor holders which utilize ratcheted retention positions for friction-based securement. The improvement may be implemented by eliminating the ratcheted retention of the second jaw member; adapting the second jaw member for continuously variable slidable engagement with the bite block; and engaging a threaded member between the second jaw member and the bite block, inclusive of the first jaw member which extends from the bite block. The threaded member within the improved sensor retention apparatus provides continuously variable adjustment of the distance between the jaw members to control retention pressure applied to the radiographic sensor. The apparatus may further be configured with alignment guides for guiding the orientation of a radiographic emission source.

An object of the invention is to provide secure retention of a radiographic sensor between the upper and lower teeth of a patient while x-ray images of dental structures are being registered.

Another object of the invention is to suitably prop open the mouth of a dental patient while performing radiographic imaging.

Another object of the invention is to provide a radiographic sensor retention apparatus having continuously variable adjustability to allow any desired retention pressure to be applied to a radiographic sensor.

Another object of the invention is to provide a radiographic sensor retention apparatus that is configured to allow for retaining radiographic sensor packages having a variety of shapes and sizes.

Another object of the invention is to provide added compliance within a radiographic sensor retention apparatus to distribute retention pressure and to prevent the sensor from slipping out of the apparatus.

Another object of the invention is to provide a radiographic sensor retention apparatus within which radiographic sensor position may be adjusted to allow sensor registration of any desired dental structures.

Another object of the invention is to provide a radiographic sensor retention apparatus that is not subject to disengagement.

Another object of the invention is to provide alignment guides for use with the radiographic sensor retention apparatus to provide a positional reference to which radiographic emission equipment may be aligned with the radiographic sensor.

Further objects and advantages of the invention will be brought out in the following portions of the specification, wherein the detailed description is for the purpose of fully disclosing preferred embodiments of the invention without placing limitations thereon.

BRIEF DESCRIPTION OF THE DRAWINGS

The invention will be more fully understood by reference to the following drawings which are for illustrative purposes only.

DETAILED DESCRIPTION OF THE INVENTION

Referring more specifically to the drawings, for illustrative purposes the present invention is embodied in the apparatus generally shown in FIG. 1 through FIG. 10. It will be appreciated that the apparatus may vary as to configuration and as to details of the parts, and that the method may vary as to the specific steps and sequence, without departing from the basic concepts as disclosed herein.

The present invention comprises an apparatus for holding a radiographic sensor positioned within the mouth of a dental patient. The sensor retention apparatus is configured for being held within the mouth of the patient in response to the biting force applied between upper and lower dental surfaces.

Figure 1:
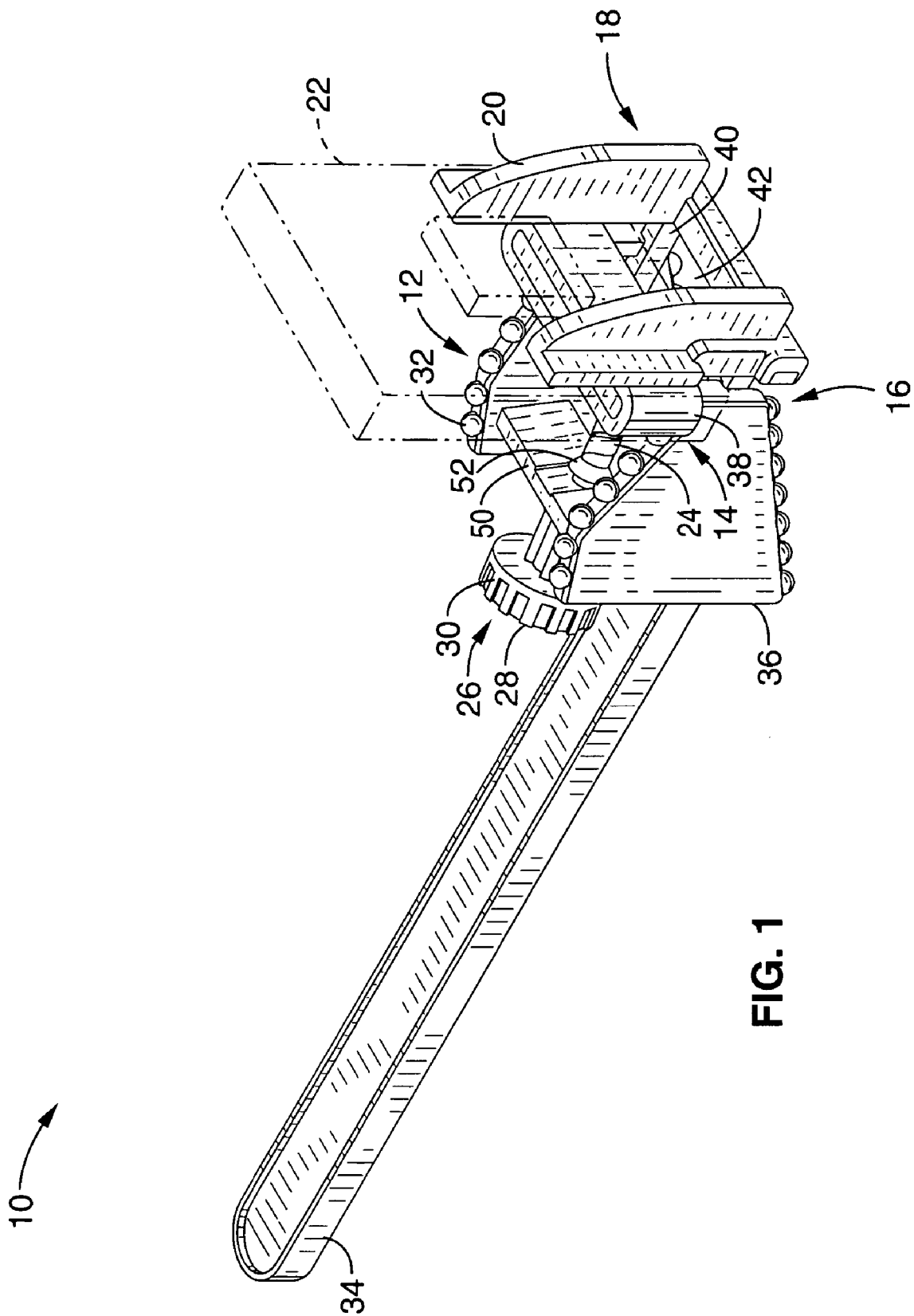
FIG. 1 is a perspective view of the radiographic sensor holder according to an embodiment of the present invention, shown with the bite block and opposing jaw member whose separation is controlled by a threaded member.
Figure 2:
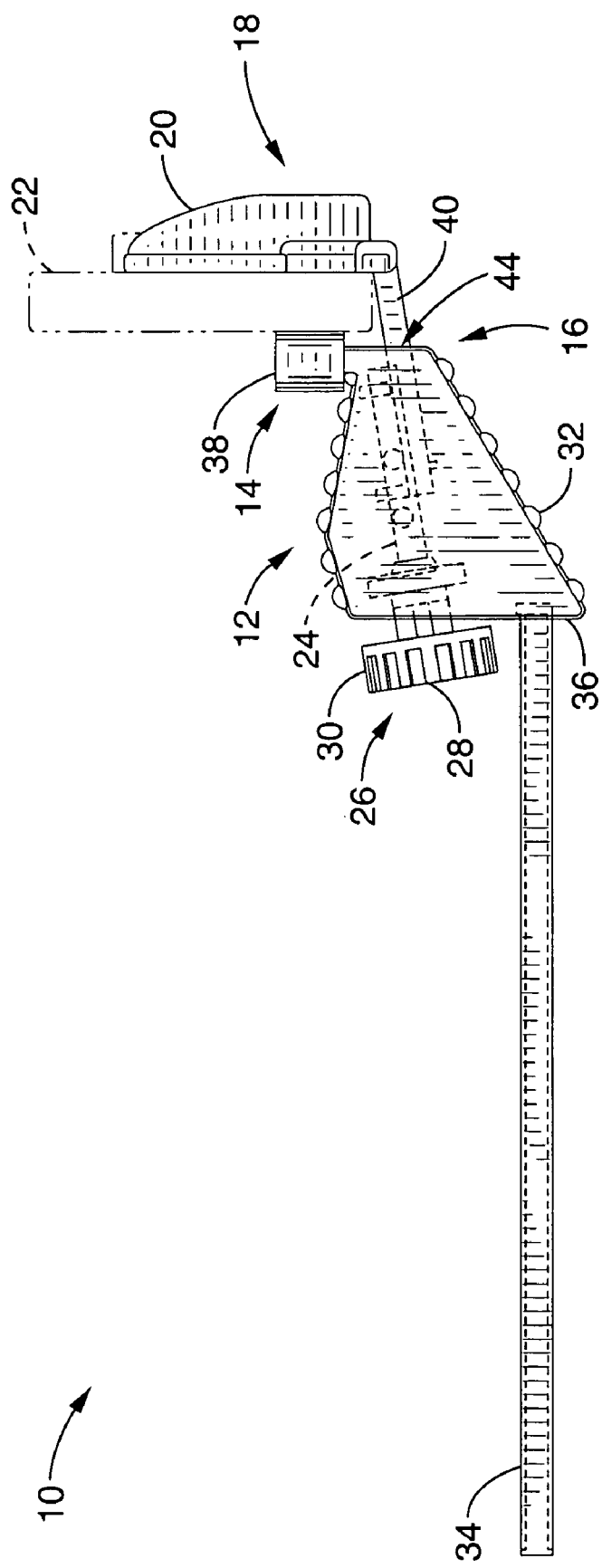
FIG. 2 is a side view of the radiographic sensor holder of FIG. 1.
Figure 3:
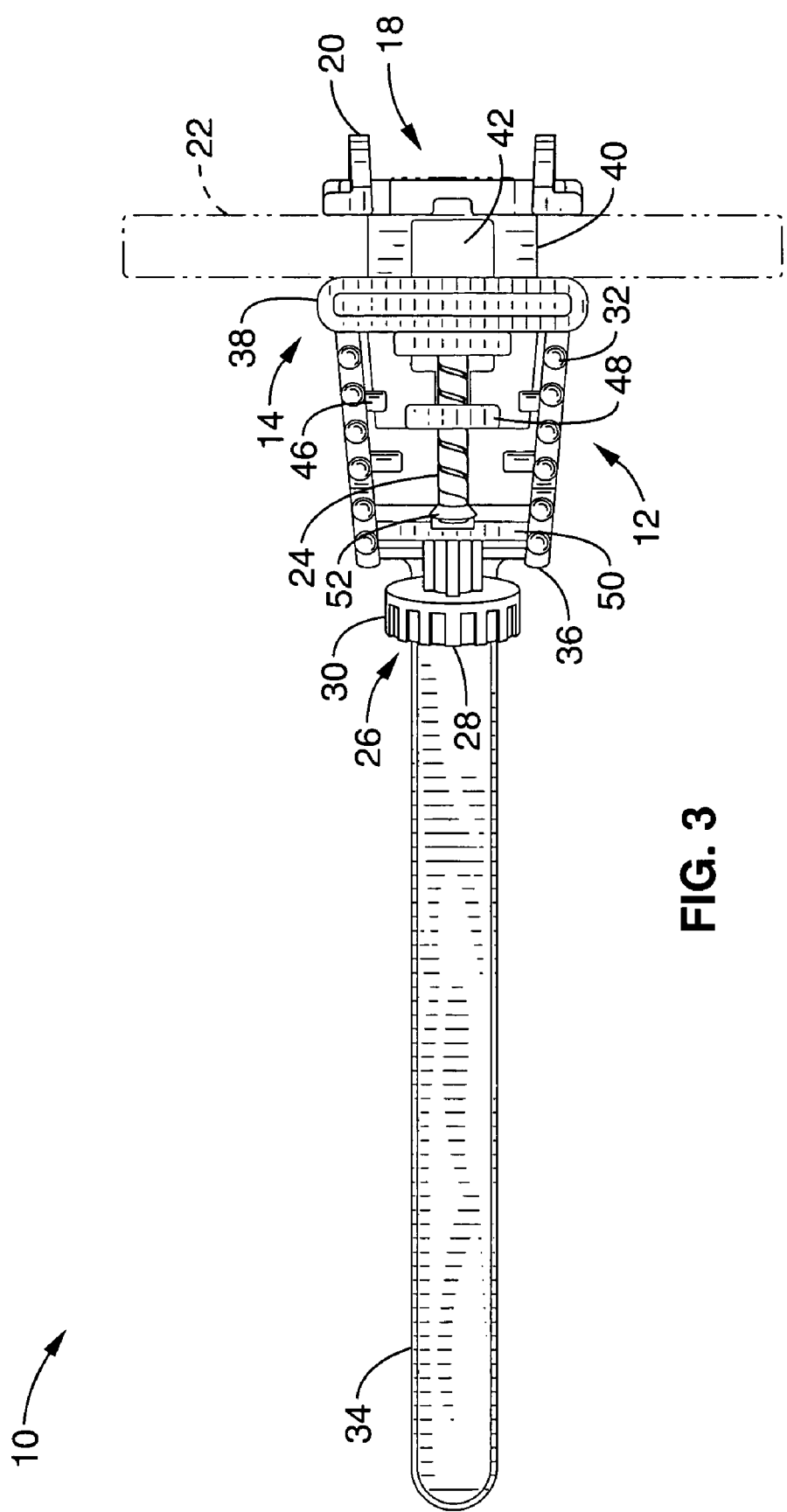
FIG. 3 is a top view of the radiographic sensor holder of FIG. 1.

FIG. 1 through FIG. 3 depict a radiographic retention apparatus 10 comprising a bite block 12 from which extends first jaw member 14 from a distal end 16 of bite block 12. A movable jaw assembly 18, is shown movably engaged with distal end 16 of bite block 12, preferably slidably engaged therein, wherein the movement of jaw assembly 18 is substantially restricted to a single axis of motion. Jaw member 20 of jaw assembly 18 is oriented in opposition to first jaw member 14 so that a radiographic sensor 22 (shown in phantom) may be retained between the first jaw member 14 and second jaw member 20. Second jaw member 20 is preferably implemented with at least two separate sections configured for engaging a sensor package having a non-planar surface, such as those having a posterior-side protrusion or similar shape irregularity, may still be securely retained between the jaws.

A threaded member 24 is shown coupled to a rotational input receiving member 26, shown as a circular head 28 having a contoured outer perimeter 30 attached to a distal end of threaded member 24. Rotational input receiving member 26 is preferably selected from the group of input receiving members for increasing torque consisting of heads, knobs, and cranks. These input receiving members being coupled to threaded member 24 to increase the torque which may be applied manually.

It will be appreciated that an indirect coupling may alternatively be provided between rotational input receiving member 26 and threaded member 24, such as gears, belts, and so forth for increasing the torque on threaded member 24. Threaded member 24 is engaged through a combination of a stationary portion and a movable portion of the apparatus. Rotation of threaded member 24 drives the position of the movable portion in relation with the stationary portion. Within the present embodiment, threaded member 24 is engaged between a threaded aperture in second jaw member 20 and a non-threaded aperture in a portion of bite block 12, such as either bite block 12 itself, or a portion of first jaw member 14 which extends therefrom. Rotation of threaded member 24 within jaw member 20 causes it to advance in relation to the fixed location of bite block 12. Leverage is provided for rotating threaded member 24 to adjust the position of second jaw member 20 by a combination of circular head 28 with contoured perimeter 30 to increase leverage.

A plurality of small protrusions 32 are shown extending from bite block 12 which are configured for engaging the biting surfaces of the teeth when the patient bites down on bite block 12. The protrusions provide for securely engaging the surfaces of dental structures to prevent inadvertent shifting of the apparatus within the patient's mouth which can create misregistration that requires capturing additional images. Each of these small protrusions is preferably circular with a rounded head extending from bite block 12 for a minimum of approximately 0.05 inches to a maximum of approximately 0.2 inches. It will be appreciated that the teeth engaging structure may be implemented in a number of ways and that alternative adaptations may be utilized for engaging the dental surfaces, such as fabricating at least portions of the bite block from compliant materials, or joining compliant (compressible) materials to one or more surfaces of the bite block.

An elongated extension 34 is shown extending from a proximal end 36 of bite block 12. Elongated extension 34 may be permanently joined to bite block 12, or bite block 12 may be adapted to allow for removable engagement of elongated extension 34 from bite block 12. Elongated extension 34 facilitates the alignment of radiographic equipment with the radiographic sensor element within sensor retention apparatus 10, and is preferable fabricated as an extension of the proximal end 36 of bite block 12. The elongated extension 34 preferably has a generally constant cross-section to facilitate slidable engagement, or other positional retention, of alignment devices at a desired position on elongated extension 34.

To distribute retention pressure and to reduce the probability of sensor package slippage, the interior of either, or both, of the jaws 14, 18, may be adapted with a compliant material, structure, or combination thereof. A preferred pressure distribution mechanism is exemplified by the use of compliant band 38 surrounding a portion of first jaw member 14. Compliant band 38 may be fabricated from any compliant material capable of being easily sterilized with the apparatus, or of being easily replaced. By way of example, the band may be fabricated from rubber, silicone, latex, or other similarly compliant materials. It will be appreciated that the inclusion of a compliant member is optional, and when utilized, it may be implemented using a variety of materials and structures without departing from the teachings herein.

Second jaw assembly 18, with jaw member 20, is movably retained in relation to bite block 12 and first jaw member 14. Second jaw assembly 18 is preferably slidably engaged with bite block 12, and the contact surfaces of jaw member 20 extend outwardly (shown substantially vertically) from a sliding member 40, which is preferably substantially planar and shown with a center cutout 42. Sliding member 40 is configured to slide through an opening 44 in bite block 12. Motion of sliding member 40 is generally constrained along a single axis of motion by a channel or deflection structure within bite block 12, such as provided by a series of separate protrusions 46 that prevent movement of the sliding member orthogonal to threaded member 24. A group of four protrusions 46 are shown above sliding member 40 in FIG. 3, with another two protrusions extending beneath sliding member 40 which are not shown in the figure. It will be recognized that restricting the motion of sliding member 40 to a single axis may be alternatively provided by employing other structural accommodations known to one of ordinary skill in the art.

A threaded aperture 48 within a portion of sliding member 40 of second jaw member 18 receives threaded member 24 for driving the motion of sliding member 40 through opening 44 in bite block 12. A second position along threaded member 24 is pivotally retained within a mounting 50 of bite block 12, wherein it may be rotated without advancing or retreating. Threaded member 24 is depicted with flanges 52 on either side of mounting 50 to prevent linear motion of threaded member 24 in mounting 50.

Alignment aids may be provided on the radiographic retention apparatus 10 to facilitate alignment of a radiographic emission unit with the radiographic sensor. It should be remembered that during use the view of the retention apparatus and retained radiographic sensor are substantially obscured, within the mouth of the patient, wherein the use of an alignment aid promotes proper orientation of the emitted rays toward the sensor. These alignment structures may be configured as permanent, removable, or a combination thereof.

By way of example, an elongated extension 34 may be provided as an extension of bite block 12. Utilizing elongated extension 34 simplifies the attachment and adjustment of alignment ring(s), arm(s), or other devices configured for attachment thereto for establishing reference positions upon which a radiographic emitter may be aligned. Elongated extension 34 is shown integrated as an extension of bite block 10, however, it may alternatively be bonded to, or removably joined to, bite block 12 to provide an alignment reference.

Figure 4:
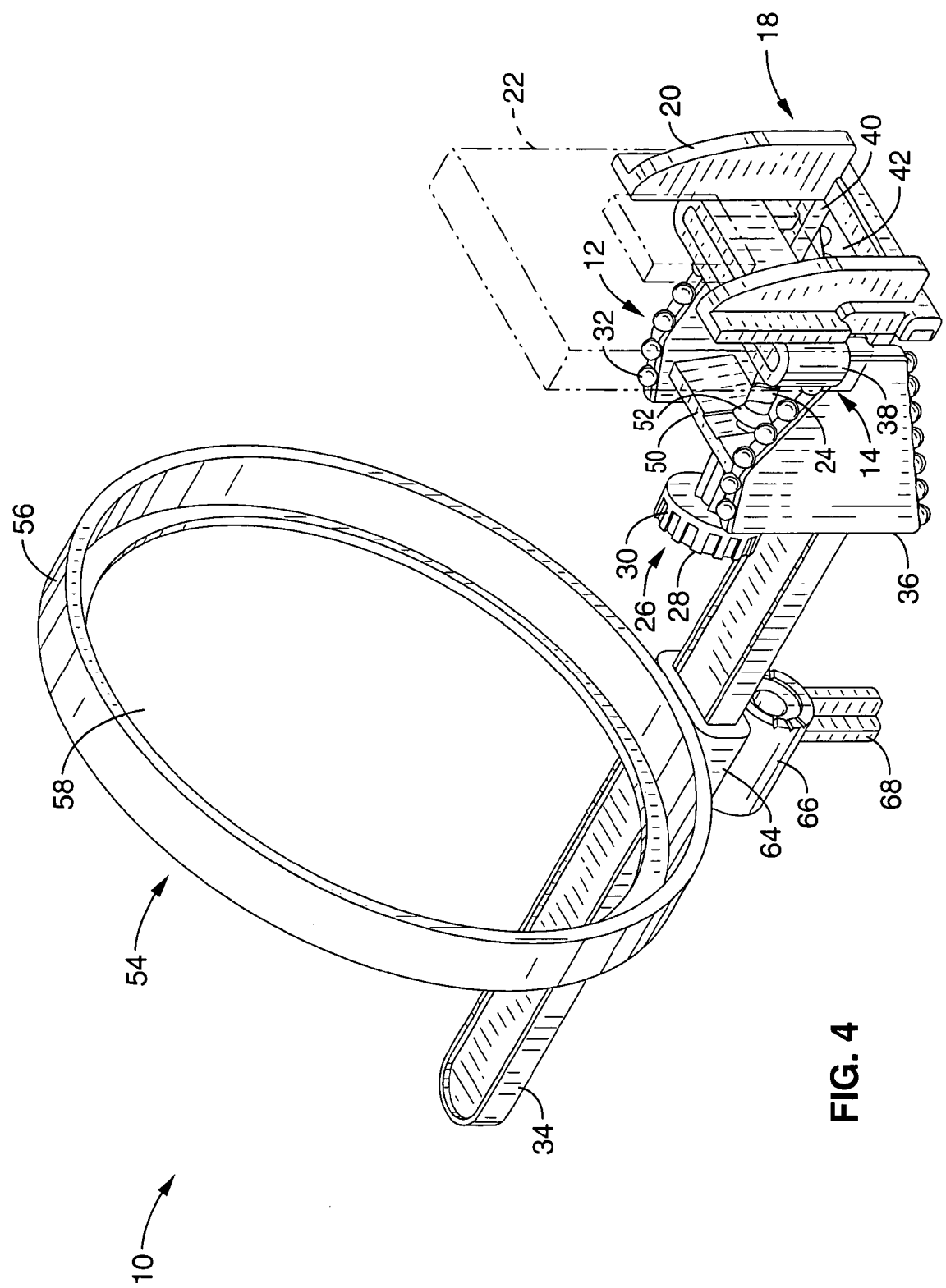
FIG. 4 is a perspective view of an alignment ring attached to an alignment guide within the radiographic sensor holder of FIG. 1 according to an aspect of the present invention.
Figure 6:
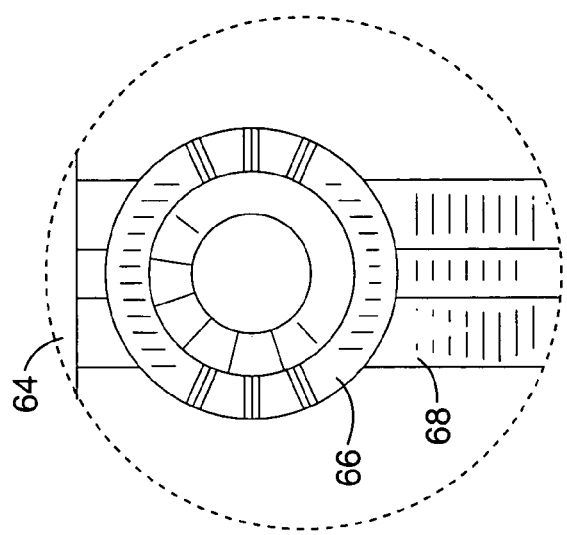
FIG. 6 is a side view of the alignment ring of FIG. 5.
Figure 5:
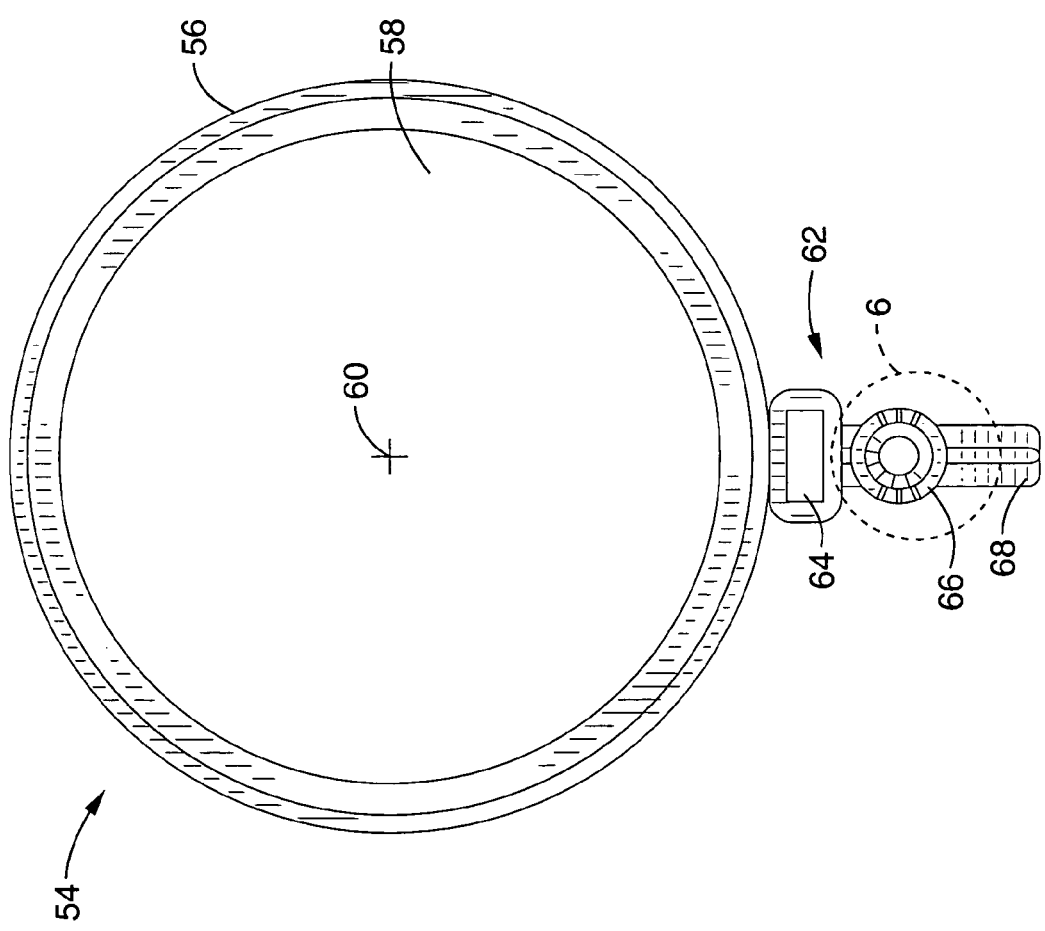
FIG. 5 is a facing view of the alignment ring of FIG. 4.
Figure 8:
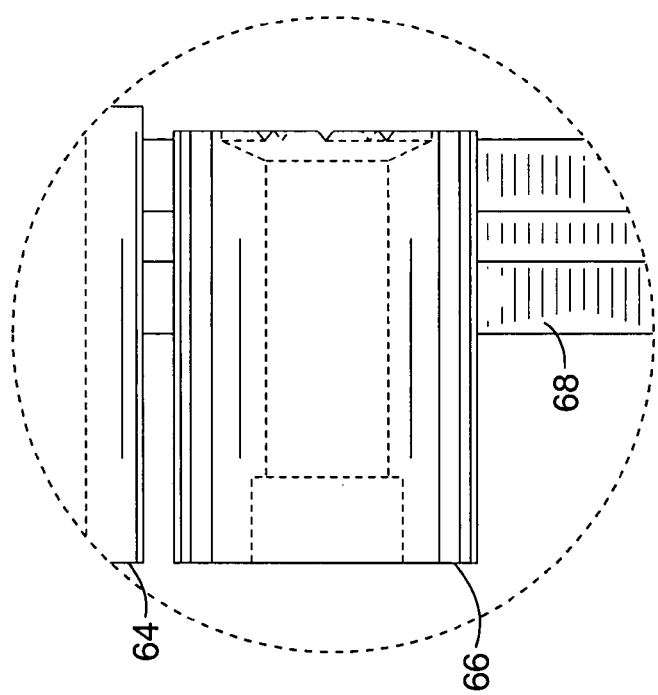
FIG. 8 is a detailed view of the mounting aperture of FIG. 7.
Figure 7:
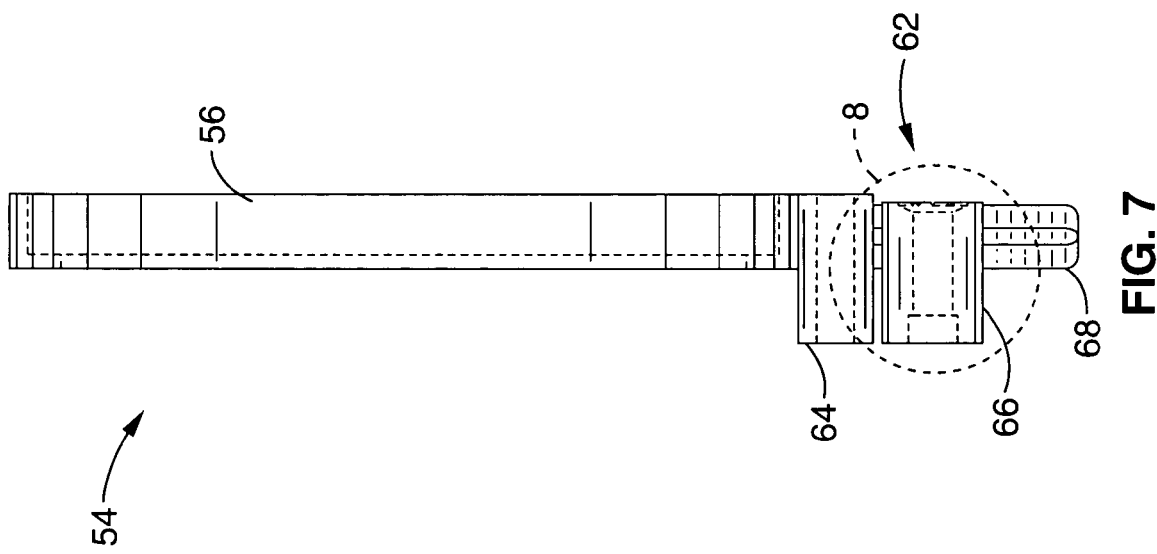
FIG. 7 is a side view of the alignment ring of FIG. 6.

FIG. 4 through FIG. 8 depict an alignment ring 54 which may be utilized for aligning radiographic emission equipment. FIG. 4 is a view of alignment ring 54 attached to the radiographic sensor holder 10, while FIG. 5 through FIG. 8 depict separate views of alignment ring 54 and associated detailed views.

Alignment ring 54 preferably comprises a substantially rigid polymeric material 56 with an alignment adaptation, such as aperture 58 having a center 60 (typically the center is open and therefore unmarked), which is configured to provide a readily recognizable reference for alignment of the radiographic equipment (not shown). It will be appreciated, for example, that aperture 58 is configured for aligning with a tubular member which typically extends from the head of a radiographic emission source, however, it will be appreciated that any number of alternative alignment systems may be supported within the present invention without departing from the teachings herein.

Alignment ring 54 is adapted with one or more engagement elements 62 or assemblies for attaching it in a fixed position in relation to bite block 12 of the radiographic sensor retention apparatus 10. One such engagement structure is exemplified by engagement aperture 64 that is adapted for being slidably engaged upon elongated extension 34. A second engagement structure 66 is shown within alignment ring 54 to provide for the attachment of additional alignment devices, such as an alignment rod. A third protruding engagement structure 68 is shown as a post to facilitate the attachment of other alignment guides or to facilitate mounting or storage of the ring. It will be readily appreciated that alignment devices, as well as the radiographic sensor holder 10 itself, may be adapted with any number and variety of alignment and mounting structures without departing from the teachings of the present invention.

Figure 9:
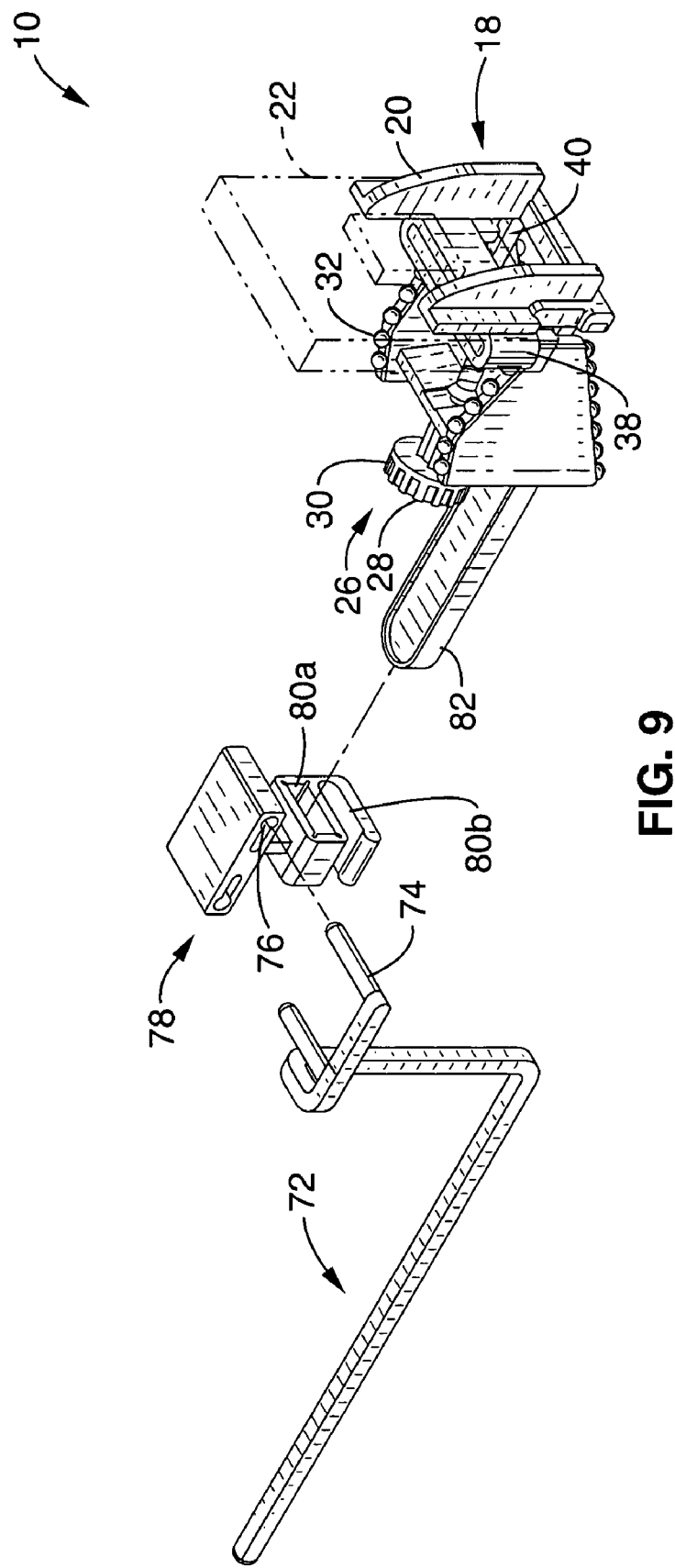
FIG. 9 is an exploded view of an alignment arm attached to a shortened alignment guide according to another embodiment of the present invention.
Figure 10:
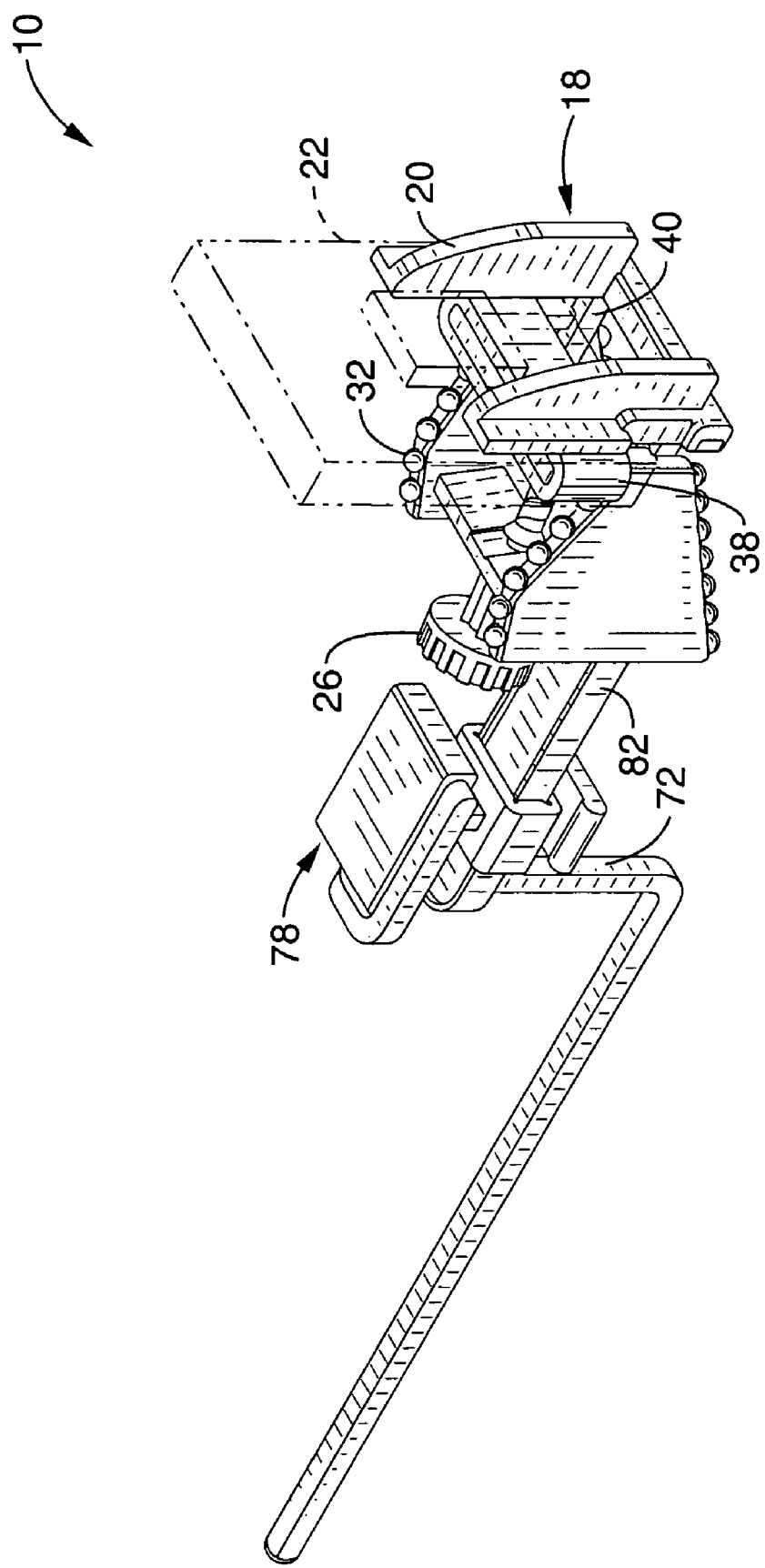
FIG. 10 is an assembled perspective view of the alignment arm attached to the alignment guide shown in FIG. 9.

FIG. 9 and FIG. 10 depict an alignment arm assembly 70 comprising an elongated arm 72 with mounting pins 74 for insertion within retention apertures 76 of engagement member 78. Alignment arm 72 is preferably fabricated of a metallic material, although other materials, such as sufficiently rigid polymers, may be alternatively utilized. Optionally, a variation of alignment arm 72 could be configured for mounting to alignment ring 54 (depicted in FIG. 4 through FIG. 6), such as inserted into aperture 66. It should be appreciated, however, that the above alignment guides are shown by way of example and that various forms of alignment devices may be connected directly to the radiographic sensor holder 10 or to other alignment guides.

Elongated extension 82 is depicted in a reduced length configuration in relation with the length of elongated extension 34 depicted previously. Elongated extension 82 may be inserted into either closed aperture 80a or open aperture 80b within engagement member 78 to orient alignment arm 72 as a position reference. Engagement member 78 is preferably fabricated from a polymeric material that is sufficiently compliant for providing a non-sliding adherence of mounting pins 74 of alignment arm 72, and the elongated extension 82 over which it may be engaged. It should be readily appreciated that the radiographic sensor retention apparatus described herein may be configured with any number of alignment guides suited to the radiographic equipment being utilized.

Accordingly, it will be seen that this invention provides a radiographic sensor retention apparatus which is continuously variably adjustable for securely retaining a radiographic sensor. The threaded retention clasp mechanism provides for infinite adjustability and ease of use. Although the retention apparatus is exemplified in a single embodiment, it should be appreciated that a number of threaded retention clasp mechanisms capable of providing continuously variable adjustment of the distance between jaw members may be implemented by one of ordinary skill in the art without departing from the teachings of the present invention. By way of example and not limitation these threaded retention clasp variations include the following: (1) Attaching the threaded member between the movable jaw member and a non-movable jaw member; (2) Using multiple jaw members which move simultaneously in response to threadable member operation; (3) Orienting the threaded member in other directions, such as with the head directed opposite the alignment arm, or in a direction requiring a motion conversion means to alter the spacing between jaws; and (4) Locating the head of the threaded member non-terminally, such as near the center of the threaded member. Furthermore, additional implementations will be obvious to one skilled in the art based on conventional design practices and the teachings contained herein.

Although the description above contains many specificities, these should not be construed as limiting the scope of the invention but as merely providing illustrations of some of the presently preferred embodiments of this invention. Therefore, it will be appreciated that the scope of the present invention fully encompasses other embodiments which may become obvious to those skilled in the art, and that the scope of the present invention is accordingly to be limited by nothing other than the appended claims, in which reference to an element in the singular is not intended to mean "one and only one" unless explicitly so stated, but rather "one or more." All structural, chemical, and functional equivalents to the elements of the above-described preferred embodiment that are known to those of ordinary skill in the art are expressly incorporated herein by reference and are intended to be encompassed by the present claims. Moreover, it is not necessary for a device or method to address each and every problem sought to be solved by the present invention, for it to be encompassed by the present claims. Furthermore, no element, component, or method step in the present disclosure is intended to be dedicated to the public regardless of whether the element, component, or method step is explicitly recited in the claims. No claim element herein is to be construed under the provisions of 35 U.S.C. 112, sixth paragraph, unless the element is expressly recited using the phrase "means for."

What is claimed is:

1. An apparatus for retaining a radiographic sensor element, comprising:
 a bite block;
 a first jaw member extending from said bite block;
 a movable second jaw member in opposition to said first jaw member; and
 means for providing variable positional adjustment of said second jaw member in relation to said first jaw member;
 wherein said means for providing variable positional adjustment comprises:
  a threaded member connecting said movable second jaw member to said first jaw member; and
  an adjustment knob attached to said threaded member for increasing the available leverage upon said threaded member.

2. An apparatus as recited in claim 1, further comprising a compliant material joined to at least one of said jaw members for distributing compression forces.

3. An apparatus as recited in claim 1, further comprising means for aligning an external radiographic emission source with said first jaw member and said second jaw member.

4. An apparatus as recited in claim 3, wherein said means for aligning external radiographic emission source comprises an elongated member extending from said bite block to provide a positional reference.

5. An apparatus as recited in claim 4, wherein said elongated member extending from said bite block is configured for the retention of at least one alignment guide.

6. An apparatus as recited in claim 5, wherein said alignment guide comprises a ring configured for slidable engagement with said elongated member.

7. An apparatus as recited in claim 5, wherein said alignment guide comprises an alignment arm assembly adapted for slidable engagement with said elongated member.

8. An apparatus as recited in claim 7, wherein said alignment arm assembly comprises:
 an engagement member adapted for engaging said alignment guide; and
 an elongated arm joined to said engagement member.

9. An apparatus as recited in claim 1, wherein the apparatus is molded from a polymeric material.

10. An apparatus as recited in claim 1, further comprising protrusions extending from said bite block which are configured for securely engaging dental structures.

11. An apparatus for retaining a radiographic sensor element for positioning within the mouth, comprising:
 a bite block;
 a first jaw member extending from said bite block;
 a movable second jaw member slidably engaged with said bite block; and
 a threaded member engaged between said second jaw member and said bite block, and configured for providing continuously variable distance adjustment for retaining a radiographic sensor between said first jaw member and said second jaw member in response to the rotation of said threaded member.

12. An apparatus as recited in claim 11, wherein said apparatus is molded from a polymeric material.

13. An apparatus as recited in claim 11, further comprising protrusions extending from said bite block that are configured for engaging dental structures.

14. An apparatus as recited in claim 13, wherein said protrusions comprise circular protrusions having a rounded head extending from said bite block.

15. An apparatus as recited in claim 14, wherein said rounded heads extend from said bite block from a minimum of approximately 0.05 inches to a maximum of approximately 0.2 inches.

16. An apparatus as recited in claim 11, wherein said second jaw member comprises at least two separate sections configured for engaging a sensor package having a non-planar surface.

17. An apparatus as recited in claim 11, further comprising compliant material joined to at least one of said jaw members.

18. An apparatus as recited in claim 17, wherein said compliant material comprises a compliant band that encircles a portion of at least one of said jaw members.

19. An apparatus as recited in claim 18, wherein said compliant band comprises a compliant band of latex or silicone based material.

20. An apparatus as recited in claim 19, wherein said compliant band is joined to said first jaw member.

21. An apparatus as recited in claim 11, further comprising a rotational input receiving member joined to said threaded member and configured for increasing rotational leverage upon said threaded member.

22. An apparatus as recited in claim 21, wherein said rotational input receiving member can be selected from the group of leverage increasing input members, consisting of heads, knobs, and cranks.

23. An apparatus as recited in claim 21, wherein said rotational input receiving member is affixed to a terminating end of said threaded member.

24. An apparatus as recited in claim 11, further comprising means for aligning an external radiographic emission unit with said first jaw member and said second jaw member.

25. An apparatus as recited in claim 24, wherein said means for aligning an external radiographic emission unit comprises an elongated member extending from said bite block to serve as a positional reference.

26. An apparatus as recited in claim 25, wherein said elongated member extending from said bite block is configured for the retention of at least one alignment guide.

27. An apparatus as recited in claim 26, wherein said alignment guide comprises a ring configured for slidable engagement upon said elongated member.

28. An apparatus as recited in claim 26, wherein said alignment guide comprises an alignment arm assembly configured for slidable engagement with said elongated member.

29. An apparatus as recited in claim 28, wherein said alignment arm assembly comprises:
 an engagement member configured for engaging said alignment guide; and
 an elongated arm joined to said engagement member.

30. An apparatus as recited in claim 29, wherein said elongated arm comprises a metallic member configured for being engaged and retained upon said engagement member.

31. An apparatus as recited in claim 30, wherein said metallic member comprises a protruding structure whose shape and size are configured for engaging a complementary mating structure within said engagement member.

32. A method for holding a dental radiographic sensor having a second jaw member which moved along a predetermined number of ratcheted positions for friction-based securement in relation to a first jaw member which extends from a bite block forming the body of said holder, comprising:
 eliminating the ratcheted retention of said second jaw member;
 configuring said second jaw member to provide continuously variable slidable engagement with said bite block; and engaging a threaded member between said second jaw member and said bite block;

wherein said threaded member is adapted for providing continuously variable adjustment of the distance between said first jaw member and said second jaw member for providing secure retention of a radiographic sensor.

33. The method as recited in claim 32, further comprising joining a rotational input receiving member to said threadable member for increasing rotational leverage upon said threadable member.

34. The method as recited in claim 33, wherein said rotational input receiving member can be selected from the group of leverage increasing input members consisting of heads, knobs, and cranks.

35. The method as recited in claim 32, further comprising a compliant cushioning member joined to at least one of said jaw members.

36. The method as recited in claim 35, wherein said cushioning member comprises a compliant band of material.

37. The method as recited in claim 36, wherein said compliant band comprises a compliant band of latex based material.

38. The method as recited in claim 36, wherein said compliant band comprises a compliant band of silicone based material.

* * * * *